United States Patent [19]

Bank et al.

[11] Patent Number: 5,616,763
[45] Date of Patent: Apr. 1, 1997

[54] ALDEHYDES AS ACCELERATORS FOR HYDROSILATION

[75] Inventors: Howard M. Bank, Freeland; Gary T. Decker, Midland, both of Mich.

[73] Assignee: Dow Corning Corporation, Midland, Mich.

[21] Appl. No.: 593,383

[22] Filed: Jan. 29, 1996

[51] Int. Cl.$^6$ ................ C07F 7/08; C07F 7/10; C07F 7/18
[52] U.S. Cl. ............ 556/479; 556/413; 556/424; 556/429; 556/438; 556/440; 556/446; 549/215
[58] Field of Search ............... 556/479, 413, 556/424, 429, 438, 440, 446; 549/215

[56] References Cited

U.S. PATENT DOCUMENTS

| | | | |
|---|---|---|---|
| 2,823,218 | 2/1958 | Speier | 260/448.2 |
| 3,220,972 | 11/1965 | Lamoreaux | 260/46.5 |
| 4,578,497 | 3/1986 | Onopchenko et al. | 556/479 |
| 5,359,111 | 10/1994 | Kleyer et al. | 556/479 |
| 5,424,470 | 6/1995 | Bank et al. | 556/479 |
| 5,449,802 | 9/1995 | Bank et al. | 556/479 |
| 5,481,016 | 1/1996 | Bank et al. | 556/479 |
| 5,486,637 | 1/1996 | Bank et al. | 556/479 |

*Primary Examiner*—Paul F. Shaver
*Attorney, Agent, or Firm*—William F. Boley

[57] ABSTRACT

A hydrosilation process where a silicon hydride is reacted with an unsaturated reactant in the presence of a platinum catalyst and an aldehyde accelerator. The aldehyde accelerators are especially useful for facilitating the hydrosilation of unsaturated reactants where the unsaturation is in the internal portion of the reactant's structure, for example, as in cyclopentene and cyclohexene.

17 Claims, No Drawings

# ALDEHYDES AS ACCELERATORS FOR HYDROSILATION

BACKGROUND OF INVENTION

The present invention is a hydrosilation process where a silicon hydride is reacted with an unsaturated reactant in the presence of a platinum catalyst and an aldehyde accelerator. The aldehyde accelerators are especially useful for facilitating the hydrosilation of unsaturated reactants where the unsaturation is in the internal portion of the reactant's structure, for example, as in cyclopentene and cyclohexene.

It is known in the art to produce organosilicon compounds by reacting a silicon hydride containing compound with an unsaturated organic compound in the presence of a catalyst. This reaction is typically referred to as hydrosilation or hydrosilylation. Typically the catalyst is platinum metal on a support, a platinum compound usually in a solvent, or a platinum complex.

In Speier et al., U.S. Pat. No. 2,823,218, a method for the production of organosilicon compounds by reacting an Si—H with a compound containing aliphatic carbon atoms linked by multiple bonds in the presence of chloroplatinic acid is taught. Lamoreaux, U.S. Pat. No. 3,220,972, teaches a similar process, however the catalyst is a reaction product of chloroplatinic acid. Lamoreux, supra, teaches the catalyst may be a complex of $PtCl_2$ and an ether and aldehyde derived from octyl alcohol.

One of the major problems known in the art with hydrosilation reactions is the de-activation of the catalyst prior to the completion of the reaction. One method for reactivation of the catalyst has been to expose the reaction mixture to oxygen. For example, Onopchenko et al., U. S. Pat. No. 4,578,497, teach the use of an oxygenated platinum containing catalyst for use in hydrosilating alkylsilanes. Kleyer et al., U.S. Pat. No. 5,359,111, disclose a method for controlling hydrosilation reaction mixtures by controlling the solution concentration of oxygen in the reaction mixture, relative to the platinum present in the reaction mixture.

In addition to the problem of de-activation of the platinum catalyst, hydrosilation processes taught in the art are not particularly effective in hydrosilating internal unsaturated bonds in organic molecules. The present inventors have unexpectedly discovered that certain aldehydes can act as accelerators for platinum catalyzed hydrosilation processes. The aldehyde accelerators are particularly effective in facilitating the hydrosilation of internal unsaturated bonds of organic molecules.

Bank et al., U.S. Pat. No. 5,424,470, teach a hydrosilation process where silicon hydride is reacted with an unsaturated reactant in the presence of platinum catalyst and an unsaturated ketone accelerator.

Bank et al., U.S. Pat. No. 5,449,802, teach a hydrosilation process where silicon hydride is reacted with an unsaturated reactant in the presence of platinum catalyst and an accelerator selected from a group consisting of acetylenic alcohols, silated acetylenic alcohols, and acetylenic ethers.

SUMMARY OF INVENTION

The present invention is a hydrosilation process where a silicon hydride is reacted with an unsaturated reactant in the presence of a platinum catalyst and an aldehyde accelerator. The aldehyde accelerators are especially useful for facilitating the hydrosilation of unsaturated reactants where the unsaturation is in the internal portion of the reactant's structure, for example, as in cyclopentene and cyclohexene.

DESCRIPTION OF INVENTION

The present invention is a hydrosilation process where a silicon hydride is reacted with an unsaturated reactant in the presence of a platinum catalyst and a novel accelerator. The hydrosilation process comprises: contacting
(A) a silicon hydride described by formula

$$R^1{}_a H_b SiX_{4-a-b}, \quad (1)$$

where each $R^1$ is independently selected from a group consisting of alkyls comprising one to about 20 carbon atoms, cycloalkyls comprising four to about 12 carbon atoms, and aryls; each X is independently selected from a group consisting of halogen and organooxy radicals described by formula $-OR^1$, where $R^1$ is as previously described, a=0 to 3, b=1 to 3, and a+b=1 to 4; and
(B) an unsaturated reactant selected from a group consisting of
  (i) substituted and unsubstituted organic compounds containing non-aromatic, unsaturated carbon-carbon bonds,
  (ii) silicon compounds comprising substituted or unsubstituted organic substituents containing non-aromatic, unsaturated carbon-carbon bonds, and
  (iii) mixtures of (i) and (ii);
in the presence of a platinum catalyst selected from a group consisting of platinum compounds and platinum complexes, and an aldehyde accelerator.

The contacting of the silicon hydride with the unsaturated reactant can be effected in standard type reactors for conducting hydrosilation processes. The contact and reaction may be run as a continuous, semi-continuous, or batch process.

Silicon hydrides which are useful in the present process are described by formula (1), where each $R^1$ is independently selected from a group consisting of alkyls comprising one to about 20 carbon atoms, cycloalkyls comprising four to about 12 carbon atoms, and aryls; a=0 to 3, b=1 to 3, and a+b=1 to 4. $R^1$ can be a substituted or unsubstituted alkyl, cycloalkyl, or aryl as described.

In formula (1) it is preferred that each $R^1$ be independently selected from a group consisting of alkyls comprising about one to six carbon atoms. Even more preferred is when each $R^1$ is methyl.

In formula 1, each X is independently selected from a group consisting of halogens and organooxy radicals described by formula $-OR^1$, where $R^1$ is as previously described. Preferred is when X is chlorine.

Examples, of silicon hydrides described by formula (1) which may be useful in the present process include trimethylsilane, dimethylsilane, triethylsilane, dichlorosilane, trichlorosilane, methyldichlorosilane, dimethylchlorosilane, ethyldichlorosilane, cyclopentyldichlorosilane, methylphenylchlorosilane, (3,3,3-trifluoropropyl)dichlorosilane, and methylmethoxychlorosilane. A preferred silicon hydride described by formula (1) is selected from a group consisting of methyldichlorosilane and dichlorosilane.

The silicon hydride is contacted with an unsaturated reactant selected from a group consisting of (i) substituted and unsubstituted organic compounds containing non-aromatic, unsaturated carbon-carbon bonds, (ii) silicon compounds comprising substituted and unsubstituted organic substituents containing non-aromatic, unsaturated carbon-carbon bonds, and (iii) mixtures of (i) and (ii). For purpose of this invention, "unsaturated" means that the compound contains at least one carbon-carbon double bond.

More specific examples of the unsaturated reactants useful in the present process include unsubstituted cycloalkene compounds comprising at least four carbon atoms, substituted cycloalkene compounds comprising at least four carbon atoms, linear alkene compounds comprising about two to 30 carbon atoms, branched alkene compounds comprising four to about 30 carbon atoms, and mixtures of two or more of any of the above.

The substituted and unsubstituted cycloalkene compounds useful in the present process are those containing one or more unsaturated carbon-carbon bonds in the ring. The unsubstituted cycloalkene compounds may be, for example, cyclobutene, cyclopentene, cyclohexene, cycloheptene, cyclooctene, cyclopentadiene, 1,3-cyclohexadiene, and 1,3,5-cycloheptatriene. Substituted unsaturated compounds useful in the present invention may be, for example, 3-methylcyclopentene, 3-chlorocyclobutene, 4-phenylcyclohexene, and 3-methylcyclopentadiene. The preferred cycloalkene compounds are cyclohexene and cyclopentene.

Other unsaturated organic compounds useful in the present process are linear and branched alkenyl compounds including, for example, compounds with terminal unsaturation such as 1-hexene and 1,5-hexadiene, compounds with internal unsaturation such as trans-2-hexene, and unsaturated aryl containing compounds such as styrene and α-methylstyrene.

The unsaturated reactants may also comprise halogen, oxygen in the form of acids, anhydrides, alcohols, esters, and ethers; and nitrogen. Mixture of two or more of the above described unsaturated organic compounds may be used in the present process.

The unsaturated organic compounds comprising halogen may include, for example, vinyl chloride, allyl chloride, allyl bromide, allyl iodide, methallyl chloride, trichloroethylene, tetrachloroethylene, tetrafluoroethylene, chloroprene, vinylidene chloride, and dichlorostyrene.

Suitable unsaturated organic compounds comprising oxygen can include, for example, ethers such as allyl and vinyl ethers; alcohols such as allyl alcohol (vinyl carbinol), methylvinylcarbinol and ethynyldimethyl-carbinol; acids such as acrylic, methacrylic, vinylacetic, oleic, sorbic, and linolenic; and esters such as vinyl acetate, allyl acetate, butenyl acetate, allyl stearate, methylacrylate, ethylcrotonate, diallyl succinate and diallyl phthalate. Suitable nitrogen containing unsaturated organic compounds include, for example, indigo, indole, acrylonitrile, and allyl cyanide.

Specifically included within the definition of unsaturated organic compounds are those substituted by organofunctional moieties such as $CH_2=CHCH_2OC(O)C(CH_3)=CH_2$, $CH_2=CHCH_2NHCH_2CH_2NH_2$, $CH_2=CHCH_2NH_2$,

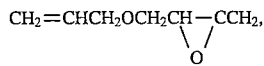

$CH_2=CHCH_2SH$    $CH_2=CHSi\{O(CH_2)_2OCH_3\}_3$, $CH_2=CHCH_2NHCH_2CH_2NHCH_2(C_6H_4)CH=CH_2$, and other similar such compounds.

The unsaturated organic compound can be a silicon compound comprising substituted and unsubstituted organic substituents as described by, for example, formulas

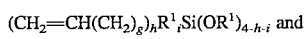 and

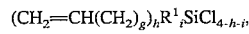

where $R^1$ is as previously described, g=0 to 12, h=1 to 3, i=0 to 3, and h+i=1 to 4.

Prior to contact of the silicon hydride with the unsaturated reactant, it may be preferable to treat or purify the unsaturated reactant. Methods useful for treating or purifying the unsaturated reactants are those known in the art for treating or purifying unsaturated organic compounds and include but are not limited to distillation and treatment with an adsorbent such as activated alumina or molecular sieves.

The relative amounts of silicon hydride and unsaturated reactant used in the present process can be varied within wide limits. Although one unsaturated carbon-carbon linkage per silicon-bonded hydrogen atom is stoichiometric, there is no requirement that the process be run under stoichiometric conditions. Generally, it is preferred that the process be run with a stoichiometric excess of silicon hydride. Preferred is when the process is run with about 0.1 to ten percent stoichiometric excess of silicon hydride. However in some situations for safety reasons it may be preferred to run the process with an excess of unsaturated reactant, for example when the silicon hydride is dichlorosilane.

The silicon hydride and unsaturated reactant are contacted in the presence of a platinum catalyst selected from a group consisting of platinum compounds and platinum complexes. Any platinum containing material which effects the reaction between the silicon hydride and an unsaturated carbon-carbon bond of the unsaturated organic compound is useful in the present invention. Examples of platinum catalysts useful in the present process are described, for example, in Onopchenko et al., U.S. Pat. No. 4,578,497; Lamoreaux, U.S. Pat. No. 3,220,972; and Speier et al., U.S. Pat. No. 2,823,218, all of which are incorporated here by reference.

The platinum catalyst can be, for example, chloroplatinic acid, chloroplatinic acid hexahydrate, Karstedt's catalyst (i.e. a complex of chloroplatinic acid with symdivinyltetramethyldisiloxane), dichlorobis(triphenylphosphine)platinum(II), cis-dichlorobis(acetonitrile)platinum(II), dicarbonyldichloroplatinum(II), platinum chloride, and platinum oxide.

A preferred platinum catalyst is selected from the group consisting of chloroplatinic acid, chloroplatinic acid hexahydrate, and platinum vinylsiloxane complexes such as a neutralized complex of chloroplatinic acid or platinum dichloride with sym-divinyltetramethyldisiloxane.

Generally, those concentrations of platinum catalyst which provide at least about one mole of platinum per billion moles of unsaturated carbon-carbon bonds added to the process by the unsaturated reactant may be useful in the present process. Concentrations of platinum catalyst providing as high as about one mole of platinum per one thousand moles of unsaturated carbon-carbon bonds added to the process by the unsaturated reactant may be useful. Higher concentrations of platinum may be used if desired. A preferred concentration of platinum catalyst is that providing about one to 1000 moles of platinum per $1\times10^6$ moles of unsaturated carbon-carbon bonds provided to the process by the unsaturated reactant.

The platinum catalyst may be dissolved in a solvent for ease of handling and to facilitate measuring the small amounts typically needed. Suitable solvents include, for example, nonpolar hydrocarbon solvents such as benzene, toluene, and xylene and polar solvents such as alcohols, ketones, glycols, and esters.

The present process is carried out in the presence of an aldehyde accelerator. The aldehyde accelerator can be, for example those aldehydes described by formula $R^2HC=O$, where $R^2$ is a monovalent hydrocarbon or organooxy radical comprising about one to 20 carbon atoms. $R^2$ can be, for example, an aryl, aralkyl, aralkenyl, cycloalkyl, cycloalkenyl, alkyl, and alkenyl. $R^2$ can be, for example, an aryl such as phenyl, tolyl, naphthyl, mesityl, xylyl, anisyl, anthryl, and methoxyphenyls; an aralkyl such as benzyl and alpha-phenyl ethyl; an aralkenyl such as betaphenyl ethenyl; a cycloalkyl comprising about four to 20 carbon atoms such as cyclopentyl and cyclohexyl; a cycloalkenyl comprising about four to 20 carbon atoms such as cyclopentenyl and cyclohexenyl; an alkyl comprising about one to twenty carbon atoms such as methyl, ethyl, t-butyl, pentyl, octyl, and eicosyl; and an alkenyl comprising about two to about 20 carbon atoms such as vinyl and pentenyl.

Examples of aldehyde accelerators useful in the present process include: benzaldehyde, mesitaldehyde, the ortho, meta, and para-isomers of anisaldehyde, 9-anthraldehyde, 2-naphthaldehyde, the ortho, meta, and para-isomers of tolualdehyde, cyclohexane-carboxaldehyde, 1,2,3,6-tetrahydrobenzaldehyde, 2,4-dimethoxybenzaldehyde, 2-phenylpropionaldehyde, amylcinnamaldehyde, and transcinnamaldehyde. A preferred aldehyde accelerator for use in the present process is benzaldehyde.

An effective concentration of the accelerator is added to the present process, where an effective concentration is one that facilitates initiation of the reaction between the silicon hydride and the unsaturated organic compound, accelerates the rate of the reaction, or reduces loss of reactivity of the catalyst in the process. A useful effective concentration of the accelerator is generally within a range of about 0.01 to 20 weight percent of the weight of the unsaturated reactant. Preferred is when the accelerator is about 0.1 to ten weight percent of the weight of the unsaturated reactant. The accelerator may be added to the process as a pre-mix with the platinum catalyst or separately.

The temperature at which the present process can be conducted can generally be within a range of about $-10°$ C. to $220°$ C. It is preferred to conduct the process at a temperature within a range of about $15°$ C. to $170°$ C. The most preferred temperature for conducting the process is within a range of about $30°$ C. to $150°$ C.

In those situations where the silicon hydride is a dihydrogendihalosilane, that is where the value for subscript b is two, it may be desirable to run the process as a two step process. In the first step of such a process the silicon hydride and unsaturated reactant are contacted in the presence of the platinum catalyst and aldehyde accelerator at a temperature which favors formation of the mono-adduct from the reaction of the silicon hydride with the unsaturated reactant. In a second step of such a process the temperature of the process is raised to a higher temperature which favors formation of the di-adduct from the reaction of the silicon hydride with the unsaturated reactant. Conduct of the first step at a lower temperature reduces disproportionation of the silicon hydride and thereby reduces byproducts. An example of such a two-step process is provided in the examples herein. Suitable temperature ranges for each step will depend upon the reactants and can be easily determined by those skilled in the art.

The following examples are provided to illustrate the present invention. These examples are not intended to limit the claims herein.

EXAMPLE 1

The ability of aldehydes to act as accelerators for the platinum catalyst hydrosilation reaction of cyclohexene with methyldichlorosilane was evaluated. A stock mixture comprising seven percent molar excess of methyldichlorosilane in cyclohexene was prepared. The cyclohexene was treated with 13× molecular sieves prior to preparation of the mixture. About $6 \times 10^{-5}$ moles of platinum, as a platinum divinylsiloxane complex, per mole of cyclohexene was added to the stock mixture. Two milliliter aliquots of the stock solution were transferred to argon-purged glass tubes and aldehyde compounds as described in Table 1 were added to the tubes at the concentrations described in Table 1. The tubes were heat sealed under argon purge and heated at $80°$ C. for three hours. At the end of three hours the tubes were cooled and the contents analyzed by gas chromatography using a thermal conductivity detector (GC-TC). The results of this analysis are reported in Table 1 as the normalized area percent of (cyclohexyl)methyldichlorosilane ($MeC_HSiCl_2$) under the GC-TC trace minus the area of the cyclohexene as 100 percent.

TABLE 1

Aldehydes as Accelerators For Hydrosilation of Cyclohexene with Methyldichlorosilane

| Aldehyde | Conc. | GLC Area % $MeC_HSiCl_2$ |
|---|---|---|
| Blank | — | 37.2 |
| Blank | — | 41.2 |
| Mesitaldehyde | 0.4 Vol. % | 98.6 |
| 9-Anthaldehyde | 0.9 Wt. % | 97.5 |
| 2-Phenylpropionaldehyde | 0.4 Vol. % | 97.5 |
| 2-Naphthaldehyde | 0.5 Wt. % | 97.4 |
| m-Anisaldehyde | 0.4 Vol. % | 97.3 |
| Cyclohexane-Carboxaldehyde | 0.4 Vol. % | 96.9 |
| Amylcinnamaldehyde | 0.4 Vol. % | 96.2 |
| 1,2,3,6-Tetrahydrobenzaldehyde | 0.4 Vol. % | 95.4 |
| Benzaldehyde | 0.4 Vol. % | 94.9 |
| 2,4-Dimethoxybenzaldehyde | 1.6 Wt. % | 93.4 |
| trans-Cinnamaldehyde | 0.4 Vol. % | 88.1 |
| o-Tolualdehyde | 0.4 Vol. % | 85.7 |
| Octyl aldehyde | 0.8 Vol. % | 67.4 |
| 5-Ethyl-2-furaldehyde | 0.4 Vol. % | 4.0 |

EXAMPLE 2

The ability of aldehydes to accelerate the reaction of dichlorosilane with cyclopentene in the presence of a platinum catalyst was evaluated. A stock mixture was prepared in an argon purged and blanketed bottle. The stock mixture comprised 15 weight percent dichlorosilane in cyclopentene. About $7 \times 10^{-4}$ moles of platinum, as a platinum divinylsiloxane complex, per mole of dichlorosilane was added to the stock mixture. Two milliliter aliquots of the catalyzed stock mixture were transferred to argon-purged glass tubes and aldehydes as described in Table 2 were added to the tubes at the concentrations described in Table 2. The tubes were heat sealed under argon purge and heated at $120°$ C. for one hour. At the end of one hour the tubes were cooled and the contents analyzed by GC-TC. The results are presented in Table 2 as the area percent of cyclopentyldichlorosilane ($C_pHSiCl_2$) and dicyclopentyldichlorosilane ($(C_p)_2SiCl_2$) under the GC-TC trace.

TABLE 2

Aldehydes as Accelerators For Hydrosilation of
Cyclopentene With Dichlorosilane

| Aldehyde | Conc. | GC-TC Area % | |
|---|---|---|---|
| | | $C_pHSiCl_2$ | $(C_p)_2SiCl_2$ |
| Blank | — | 11.7 | 0.3 |
| m-Anisaldehyde | 1.0 Vol. % | 13.5 | 3.8 |
| Cyclohexane-carboxaldehyde | 1.0 Vol. % | 18.3 | 0.0 |
| 2,4-Dimethoxybenzaldehyde | 0.9 Wt. % | 15.6 | 0.0 |
| trans-Cinnamaldehyde | 1.0 Vol. % | 19.0 | 0.0 |
| 9-Anthraldehyde | 1.1 Wt. % | 20.2 | 0.0 |
| 2-Phenylpropionaldehyde | 1.0 Vol. % | 19.3 | 0.0 |
| Benzaldehyde | 1.0 Vol % | 1.0 | 17.7 |

EXAMPLE 3

The effect of benzaldehyde and dichlorosilane concentrations on the platinum catalyzed hydrosilation of cyclopentene with dichlorosilane was evaluated. Mixtures of dichlorosilane and cyclopentene were prepared in argon purged and blanketed bottles. The weight percent of dichlorosilane in each mixture is described in Table 3. A platinum divinylsiloxane complex was added to the mixture to provide the concentrations of platinum described in Table 3. The concentration of platinum is described as the moles of platinum per mole of dichlorosilane present in the mixture. Two milliliter aliquots of the catalyzed mixture were transferred to argon-purged glass tubes and benzaldehyde was added at the concentration described in Table 3 (BZAL Conc.). The tubes were heat sealed under argon purge and heated at 120° C. for one hour. At the end of the one hour, the tubes were cooled and analyzed by GC-TC. The results are presented in Table 3 as the area percent of cyclopentyldichlorosilane ($C_pHSiCl_2$) and dicyclopentyldichlorosilane (($C_p)_2SiCl_2$) under the GC-TC trace.

TABLE 3

Effect of Benzaldehyde and Dichlorosilane Concentrations on
Hydrosilation of Cyclopentene with Dichlorosilane

| Run | Pt Conc. (Mole Pt/Mole Si) | BZAL Conc. (Vol. %) | $H_2SiCl_2$ (Wt. %) | GC-TC Area % | |
|---|---|---|---|---|---|
| | | | | $C_pHSiCl_2$ | $(C_p)_2SiCl_2$ |
| 1[a] | 7 × 10⁻⁴ | — | 29.9 | 32.6 | 1.3 |
| 2 | 7 × 10⁻⁴ | 0.5 | 15 | 23.1 | 1.8 |
| 3 | 7 × 10⁻⁴ | 1.0 | 15 | 7.0 | 19.8 |
| 4 | 7 × 10⁻⁴ | 1.5 | 15 | 0.8 | 24.3 |
| 5 | 7 × 10⁻⁴ | 1.0 | 18.4 | 2.1 | 25.7 |
| 6[a] | 7 × 10⁻⁴ | 2.0 | 29.9 | 3.5 | 37.1 |

[a]Sample heated at 50° C. for 30 minutes then at 120° C. for 60 minutes.

EXAMPLE 4

The effect of aldehyde structure and temperature on the platinum catalyzed hydrosilation of cyclopentene with dichlorosilane was evaluated. Stock mixtures containing either 13 weight percent or 15 weight percent dichlorosilane in cyclopentene as described in Table 4 were prepared in argon purged and blanketed bottles. About 7×10⁻⁴ moles of platinum, as a platinum divinylsiloxane complex, per mole of dichlorosilane was added to the bottle. Two milliliter aliquots of the catalyzed mixture were transferred to argon-purged glass tubes and aldehydes as described in Table 4 were added to the tubes at the concentrations described in Table 4. The tubes were heat sealed and heated for one hour at the temperatures described in Table 4. At the end of the one hour the tubes were cooled and the contents analyzed by GC-TC. The results are presented in Table 2 as the area percent of cyclopentyldichlorosilane ($C_pHSiCl_2$) and dicyclopentyldichlorosilane (($C_p)_2SiCl_2$) under the GC-TC trace.

TABLE 4

Effect of Aldehyde Structure and Temperature on
Hydrosilation of Cyclopentene With Dichlorosilane

| Aldehyde | Aldehyde (Vol. %) | $H_2SiCl_2$ (Wt. %) | Temp. (°C.) | GC-TC Area % | |
|---|---|---|---|---|---|
| | | | | $C_pHSiCl_2$ | $(C_p)_2SiCl_2$ |
| Blank | — | 13 | 100 | 22.3 | 0.5 |
| Benzaldehyde | 1.5 | 13 | 100 | 6.6 | 22.3 |
| m-Anisaldehyde | 2.0 | 13 | 100 | 24.1 | 2.8 |
| o-Anisaldehyde | 2.0 | 13 | 100 | 22.8 | 0.6 |
| p-Anisaldehyde | 2.0 | 13 | 100 | 17.2 | 10.9 |
| Blank | — | 15 | 120 | 18.2 | 0.0 |
| Benzaldehyde | 1.5 | 15 | 120 | 1.2 | 25.5 |
| m-Anisaldehyde | 2.0 | 15 | 120 | 3.8 | 22.8 |
| o-Anisaldehyde | 2.0 | 15 | 120 | 17.8 | 3.5 |
| p-Anisaldehyde | 2.0 | 15 | 120 | 1.7 | 20.7 |

EXAMPLE 5

The ability of benzaldehyde to accelerate the reaction of dichlorosilane with cyclopentene in the presence of a platinum catalyst using a two-step process was evaluated. A stock mixture comprising 28.5 weight percent dichlorosilane in cyclopentene was prepared in an argon purged and blanketed bottle. Two milliliter aliquots of this stock mixture were placed in argon purged glass tubes containing a sufficient amount of a platinum divinylsiloxane complex to provide a final platinum concentration of 7×10⁻⁴ moles per mole of dichlorosilane. Where indicated benzaldehyde, or for reference purposes 2-methyl-3-butyn-2-ol (MBO), was added to the tubes as an accelerator. The concentration of accelerator was 2 volume percent, based upon total volume present in the tube. The tubes were cooled in an IPA/dry ice bath and heat sealed under an argon blanket. In the first-step the tubes where heated at 50° C. for 30 minutes. In the second step the tubes were heated at 120° C. for 60 minutes. The tubes were cooled and the contents analyzed by GC-TC. The results of this analysis are reported in Table 5 as the percent area under the GC-TC trace.

TABLE 5

| Aldehyde | Step-One Time/Temp. | Step-Two Time/Temp. | GC-TC Area % | | |
|---|---|---|---|---|---|
| | | | $H_2SiCl_2$ | $CpHSiCl_2$ | $Cp_2SiCl_2$ |
| Blank | 0.5 h/50° C. | — | 0.3 | 38.9 | 0.0 |
| Blank | 0.5 h/50° C | 1 h/120° C. | 0.0 | 14.8 | 30.8 |
| MBO | 0.5 h/50° C. | — | 0.0 | 37.1 | 1.7 |
| MBO | 0.5 h/50° C. | 1 h/120° C. | 0.0 | 1.0 | 48.7 |
| BZAL | 0.5 h/50° C. | — | 0.0 | 30.4 | 4.7 |
| BZAL | 0.5 h/50° C. | 1 h/120° C. | 0.0 | 6.7 | 41.9 |

We claim:

1. A hydrosilation process comprising: contacting (A) a silicon hydride described by formula

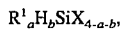

$$R^1_a H_b SiX_{4-a-b},$$

where each $R^1$ is independently selected from a group consisting of alkyls comprising one to about 20 carbon atoms, cycloalkyls comprising four to about 12 carbon atoms, and aryls; each X is independently selected from a group consisting of halogen and organooxy radicals described by formula —$OR^1$, where $R^1$ is as previously described, a=0 to 3, b=1 to 3, and a+b=1 to 4; and (B) an unsaturated reactant selected from a group consisting of
   (i) substituted and unsubstituted organic compounds containing non-aromatic, unsaturated carbon-carbon bonds,
   (ii) silicon compounds comprising substituted or unsubstituted organic substituents containing non-aromatic, unsaturated carbon-carbon bonds, and
   (iii) mixtures of (i) and (ii);

in the presence of a platinum catalyst selected from a group consisting of platinum compounds and platinum complexes, and an aldehyde accelerator.

2. A process according to claim 1, where $R^1$ is methyl.
3. A process according to claim 1, where X is chlorine.
4. A process according to claim 1, where the silicon hydride is selected from a group consisting of methyldichlorosilane and dichlorosilane.
5. A process according to claim 1, where the unsaturated reactant is selected from a group consisting of cyclohexene and cyclopentene.
6. A process according to claim 1, where the unsaturated reactant is cyclohexene.
7. A process according to claim 1, where the unsaturated reactant is contacted with a stoichiometric excess of the silicon hydride.
8. A process according to claim 1, where the unsaturated reactant is contacted with about 0.1 to ten percent stoichiometric excess of the silicon hydride.

9. A process according to claim 1, where the platinum catalyst is selected from a group consisting of chloroplatinic acid, chloroplatinic acid hexahydrate, and platinum vinylsiloxane complexes.
10. A process according to claim 1, where the concentration of the platinum catalyst is about one to 1000 moles of platinum per $1 \times 10^6$ moles of non-aromatic unsaturated carbon-carbon bonds provided to the process by the unsaturated reactant.
11. A process according to claim 1, where concentration of the accelerator is within a range of about 0.01 to 20 weight percent of the weight of the unsaturated reactant.
12. A process according to claim 1, where concentration of the accelerator is within a range of about 0.1 to ten weight percent of the weight of the unsaturated reactant.
13. A process according to claim 1, where the silicon hydride is contacted with the unsaturated reactant at a temperature within a range of about 15° C. to 170° C.
14. A process according to claim 1, where the silicon hydride is methyldichlorosilane, the unsaturated reactant is cyclohexene, the platinum catalyst is a platinum vinylsiloxane complex, and the accelerator is benzaldehyde.
15. A process according to claim 1, where the silicon hydride is dichlorosilane, the unsaturated reactant is cyclopentene, the platinum catalyst is a platinum vinylsiloxane complex, and the accelerator is benzaldehyde.
16. A process according to claim 1, where the aldehyde accelerator is selected from a group consisting of mesitaldehyde, 9-anthaldehyde, 2-phenylpropionaldehyde, 2-naphthaldehyde, m-anisaldehyde, o-anisaldehyde, p-anisaldehyde, cyclohexanecarboxaldehyde, amylcinnamaldehyde, 1,2,3,6-tetrahydrobenzaldehyde, benzaldehyde, 2,4-dimethoxybenzaldehyde, trans-cinnamaldehyde, o-tolualdehyde, and octyl aldehyde.
17. A process according to claim 1, where the silicon hydride is a dihydrogendihalosilane and the process is run as a two-step process with the contact of the first-step being at a temperature which favors formation of a mono-adduct from the reaction of the silicon hydride with the unsaturated reactant and the contact of the second-step being at a higher temperature which favors formation of a di-adduct from the reaction of the silicon hydride with the unsaturated reactant.

* * * * *